US012778391B2

(12) United States Patent
Buch

(10) Patent No.: US 12,778,391 B2
(45) Date of Patent: Nov. 3, 2026

(54) ENDOSCOPE PACKAGING SYSTEM COMPRISING AN ENDOSCOPE AND A PROTECTIVE SHEATH PART

(71) Applicant: AMBU A/S, Ballerup (DK)

(72) Inventor: Ken Henrik Buch, Vordingborg (DK)

(73) Assignee: AMBU/AS, Ballerup (DK)

( * ) Notice: Subject to any disclaimer, the term of this patent is extended or adjusted under 35 U.S.C. 154(b) by 191 days.

(21) Appl. No.: 18/745,079

(22) Filed: Jun. 17, 2024

(65) Prior Publication Data

US 2024/0423453 A1 Dec. 26, 2024

(30) Foreign Application Priority Data

Jun. 23, 2023 (DE) ........................ 102023116575.5

(51) Int. Cl.
*A61B 1/00* (2006.01)
*A61B 1/005* (2006.01)

(52) U.S. Cl.
CPC ...... *A61B 1/00144* (2013.01); *A61B 1/00135* (2013.01); *A61B 1/0055* (2013.01)

(58) Field of Classification Search
CPC ............ A61B 1/00144; A61B 1/00135; A61B 1/0055; A61B 1/00142; A61B 1/00137
See application file for complete search history.

(56) References Cited

U.S. PATENT DOCUMENTS 1,120,549 A * 12/1914 Schellberg .......... A61M 25/002 206/364
3,595,230 A * 7/1971 Suyeoka ........... A61M 25/0612 604/171
3,709,223 A * 1/1973 Macalalad ......... A61M 25/0111 604/162
4,646,722 A 3/1987 Silverstein et al.
5,386,816 A 2/1995 Inoue et al.
(Continued)

FOREIGN PATENT DOCUMENTS

DE 69215639 T2 6/1997
EP 0184778 B1 7/1991
(Continued)

OTHER PUBLICATIONS

German Search Report received from German patent application No. 10 2023 116 575.5 mailed on Mar. 25, 2024, 12 pages (6 pages English Translation and 6 pages original copy).
(Continued)

*Primary Examiner* — Chun Hoi Cheung
(74) *Attorney, Agent, or Firm* — Faegre Drinker Biddle & Reath LLP

(57) ABSTRACT

The present disclosure relates to an endoscope packaging system (1). The endoscope packaging system (1) has an endoscope (2) comprising: an endoscope handle or interface (4); and an insertion cord (6) configured to be inserted into a patient's body cavity and comprising an bending section and a distal tip (12), the bending section comprising a plurality of bending segments (31) made from a polymer material; and a protective sheath part (34) configured to accommodate at least the distal tip (12) and the bending section of the insertion cord (6) of the endoscope (2) and configured to keep the bending section (10) straight during storage and transport.

19 Claims, 4 Drawing Sheets

(56) References Cited

U.S. PATENT DOCUMENTS

| | | | | |
|---|---|---|---|---|
| 5,415,157 | A | 5/1995 | Welcome | |
| 6,551,238 | B2 | 4/2003 | Staud | |
| 9,398,839 | B2 | 7/2016 | Rehe | |
| 10,874,287 | B2 * | 12/2020 | Ouyang | A61B 1/0684 |
| 12,342,985 | B2 * | 7/2025 | McCabe | A61B 1/122 |
| 2002/0068028 | A1 * | 6/2002 | Hight, III | A61B 1/121 422/294 |
| 2008/0251102 | A1 * | 10/2008 | Haack | B08B 9/023 15/104.93 |
| 2013/0267778 | A1 * | 10/2013 | Rehe | A61B 1/00096 600/125 |
| 2014/0343361 | A1 * | 11/2014 | Salman | A61B 1/0615 600/125 |
| 2015/0068939 | A1 * | 3/2015 | Seitz, III | A61B 46/10 206/363 |
| 2020/0015662 | A1 * | 1/2020 | Kaye | A61B 1/00131 |
| 2021/0378492 | A1 | 12/2021 | McCabe | |

FOREIGN PATENT DOCUMENTS

| | | | |
|---|---|---|---|
| EP | 2647330 | A1 | 10/2013 |
| FR | 3066899 | A1 | 12/2018 |
| JP | 2007-075281 | A | 3/2007 |
| JP | 04-682090 | B2 | 5/2011 |

OTHER PUBLICATIONS

NPL Endoguard 2023, https://medicpart.de/Endoguard/ archived in http://www.archive.org Mar. 20, 2023 [downloaded Mar. 25, 2024], and English equivalent.

The Wayback Machine, "Schützen Sie Ihre Endoskope," EndoGuard®, Mar. 25, 2024, pp. 1-7.

* cited by examiner

ENDOSCOPE PACKAGING SYSTEM COMPRISING AN ENDOSCOPE AND A PROTECTIVE SHEATH PART

CROSS-REFERENCE TO RELATED APPLICATIONS

This application claims priority from and the benefit of German Patent Application No. 10 2023 116 575.5, filed Jun. 23, 2023; the disclosure of said application is incorporated by reference herein in its entirety.

TECHNICAL FIELD

The present disclosure relates to an endoscope packaging system including an endoscope and a protective sheath part.

BACKGROUND

Endoscopes, including specialized versions thereof such as bronchoscopes, arthroscopes, colonoscopes, laparoscopes, gastroscopes, duodenoscopes, and ureteroscopes, are well known from the related art and are used for visual examination and diagnosis of hollow organs and body cavities, as well as to assist in surgery, e.g. for a targeted tissue sampling. Both reusable and disposable (i.e. single-use) endoscopes are known. Known endoscopes usually comprise an endoscope handle via which an operator/user can hold and control the endoscope. An insertion cord comprising an insertion tube, an actively bendable bending section, which is a section of increased flexibility relative to the insertion tube, and a distal tip unit is usually connected to the endoscope handle. The insertion cord is configured to be inserted into the hollow organs and body cavities of a patient. The distal tip unit often comprises an optical module or a camera module for visual examination of hollow organs and body cavities.

Known endoscopes often contain steering wires that are pulled and released to bend the bending section of the endoscope, in order to tilt the distal tip, said pulling and releasing actively bending the bending section (vs. happenstance or uncontrolled bending). In order to actively bend the bending section, a rotating force being applied to e.g. a handle wheel or a lever provided at the proximal endoscope handle by a user may be transmitted into a pulling force acting on the steering wires in an axial direction of the steering wires and via the steering wires on the bending section.

Insertion cords of known endoscopes may be long and thin. When the endoscopes are stored, transported or shipped to the customer or user, the endoscopes are usually packed in a packaging system. The packaging system may comprise a sterile packaging or barrier part, preferably a (semipermeable) foil, in which the endoscope is shrink-wrapped into. Because of its length, there is the danger that the insertion cord is bent or folded in the packaging system. Single-use endoscopes with bending sections made from polymer material are especially in danger of (permanent) deformation of the bending section because of the transport or storage in a folded or bent state. The bending section may form a curve because of ageing of the polymer material of the bending section. Furthermore, the steering wires of the endoscope may provide a tensile strain on the bending section, resulting in a permanent bending of the bending section during transport and storage. Especially thin hinge members of the bending section may be deformed or bent. When a user or surgeon opens the packaging system at the side of the operation, a deformed bending section may give the appearance of a low quality endoscope.

Relative movement between the distal tip of the endoscope and the packaging material may cause the distal tip unit, and especially the camera module in the distal tip unit, to bump against the packaging. This may especially happen when the endoscope packaging system is dropped or rapidly moved by the user. There is a risk that such repeated bumping may result in damage of the camera module of the distal tip unit.

BRIEF DESCRIPTION OF THE DISCLOSURE

The tasks and objectives of the present disclosure are to eliminate or at least reduce the disadvantages of the related art. In particular, an endoscope packaging system shall be provided which reduces deformation of a bending section of an endoscope during storage and transport and protects a distal tip unit of the endoscope against damages. Furthermore, the endoscope packaging system should be cost-effective and easy to manufacture to be suitable for use in single-use endoscopes.

The present disclosure relates to an endoscope packaging system comprising an endoscope and a protective sheath part. The endoscope comprises an endoscope handle or interface and an insertion cord configured to be inserted into a patient's body cavity and comprising an actively bendable bending section and a distal tip unit, the bending section comprising a plurality of bending segments made from a polymer material. The protective sheath part is configured to accommodate at least the distal tip unit and the bending section and is configured to keep the bending section straight during storage and transport.

Keeping the bending section straight may be understood such that the protective sheath part may be configured to surround the distal tip unit and the bending section (in a circumferential direction of the bending section) and may avoid an (unwanted) folding, curving or bending or generally relative movement of the bending section with regards to the protective sheath part. A straight bending section may be defined in this context as a bending section essentially without a curvature. Thus, the protective sheath part may comprise an (inner) size or shape that is adapted to the (outer) size or shape of the distal tip unit and the bending section. Thus, the protective sheath part keeps the bending section and the distal tip unit of the endoscope straight after they have been inserted into the protective sheath part.

The endoscope according to the present disclosure may preferably be a single-use endoscope, which is intended to be disposed of after use. This means that the endoscope is preferably optimized for one single use. The endoscope preferably has a limited number of elements, which are preferably manufactured with polymer materials, e.g. by injection molding, and which can be easily assembled. Compared to reusable endoscopes, a single-use endoscope is only used once and thus does not have to withstand rather aggressive cleaning or sterilization processes and general harsh handling over the life cycle of the endoscope.

Preferably, the insertion cord of the endoscope is connected to the endoscope handle or interface and comprises an insertion tube, the bending section and the distal tip unit extending in this order in the proximal-distal direction. The distal tip unit may comprise a camera module or imaging device. The bending section is preferably actively bendable by a number of steering wires. The bending section of the endoscope may comprise the plurality of bending segments made from a polymer or plastic material. The plurality of bending segments may be connected by (thin) bendable hinges or hinge members that function as (small/thin) material bridges between the bending segments. The hinges may also be made from a polymer or plastic material. The bending section and the distal tip unit of the endoscope are preferably inserted into the protective sheath part.

The endoscope packaging system according to the present disclosure has the following advantages. The protective sheath part covers and protects the bending section and the distal tip unit. During transport or storage of the endoscope packaging system, the protective sheath part minimizes or prevents relative movement of the bending section and the distal tip unit. Therefore, the protective sheath part minimizes the danger of damage to the distal tip unit and especially to the camera module or optical module in the distal tip unit. Furthermore, the protective sheath part prevents (unwanted) bending of the bending section. The protective sheath part keeps the bending section straight. Especially, permanent deformation of the bending section during storage and transport may be prevented by the protective sheath part. This results in a new and undeformed endoscope despite the storage of the endoscope in the packaging.

Preferably, the bending section may have an outer circumference and the protective sheath part may have an inner circumference. The inner circumference of the protective sheath part may be adapted in size and shape to the outer circumference of the bending section so that the bending section is kept straight when accommodated in the protective sheath part.

Said differently, the form and the dimensions of the protective sheath part may be configured to receive the bending section and fit the (outer) form and dimensions of the bending section. The fitting or fitted protective sheath part may surround the bending section and may minimize relative movement between the protective sheath part and the bending section. The protective sheath part further keeps the bending section straight or in an extended (not bent) state and thus prevents or at least minimizes permanent deformation of the bending section or its bending segments and/or hinges during storage and transport. The minimized relative movement of the endoscope in the protective sheath part and especially of the distal tip unit may result in an improved protection of the distal tip unit. Thus, the camera module or optical system in the distal tip unit may be protected by the fitting protective sheath part.

According to a preferred aspect of the present disclosure, the protective sheath part may form a hole or channel for the insertion of the distal tip unit and the bending section. The hole or channel of the protective sheath part may be configured to receive both the distal tip unit and the bending section of the endoscope and may have an inner diameter/circumference adapted in size and shape to the outer diameter/circumference of the bending section. Said differently, the protective sheath part may at least comprise an (elongated) tube portion or element forming the hole or channel for the insertion of the distal tip unit and the bending section. During packaging of the endoscope, the distal tip unit and the bending section may slide into the hole or channel of the protective sheath part. The hole or channel may keep the bending section straight.

Preferably, the protective sheath part may form or comprise a stop configured to prevent further insertion of the distal tip unit and the bending section, when the distal tip unit reaches the stop. During insertion of the distal tip unit and the bending section into the protective sheath part, the stop may stop or limit the insertion in an axial insertion direction. Thus, the stop may form an end wall of the protective sheath part limiting the insertion movement of the distal tip unit. The (axial) stop may receive or surround the distal tip unit and protect the optical module or camera module at the distal tip unit against damage or relative movement.

According to a preferred aspect of the present disclosure, the distal tip unit and the bending section may have an axial length in an axial direction of the insertion cord. Furthermore, the protective sheath part may have an axial length, and the axial length of the protective sheath part may be longer than or as long as the axial length of the distal tip unit and the bending section and may be shorter, in particular significantly shorter, than an axial length or the entire insertion cord. Therefore, the protective sheath part may cover the combined length of the bending section and the distal tip unit. Thus, the complete bending section and the distal tip unit may be protected by the protective sheath part. The bending section may be kept straight by the protective sheath part while the distal tip unit may be protected against damage and sudden movements. However, it may not be necessary to insert the whole insertion cord into the protective sheath part, as the bending section may be the section of the insertion cord mostly affected by unwanted deformation or bending. Therefore, according to an especially preferred aspect, the axial length of the protective sheath part is maximum 50%, preferably maximum 30%, especially preferred maximum 10% longer than the combined axial length of the distal tip unit and the bending section.

Preferably, the endoscope packaging system may further comprise a protection pipe configured to receive and accommodate the insertion cord of the endoscope and the protective sheath part. The protection pipe may be formed as a tubular pipe or a tube, preferably made from a transparent polymer or plastic material, and may comprise a distal opening and a proximal opening. At least a section of the insertion cord of the endoscope, preferably essentially the entire insertion cord, may be inserted into the protection pipe. The protection pipe may protect the (section of the) insertion cord against damage during the storage and transport of the endoscope. It is to be added that the protection pipe is not essential for the present disclosure, since the advantageous effects of the disclosure are reached by the interaction of the endoscope and the protective sheath part.

In case a protection pipe is provided, the protective sheath part may be an insert inserted into the protection pipe and arranged radially between the insertion cord of the endoscope and the protection pipe. Said differently, the protection pipe may be configured to receive the protective sheath part. The protective sheath part may be inserted or pushed into the protection pipe from a distal side or direction. The distal side or direction in this context may be understood as the side of the protection pipe in which the distal tip unit of the endoscope is positioned when the endoscope is inserted (completely) into the packaging system. Thus, the protective sheath part may be inserted or pushed into the protection pipe from the distal opening. An (outer) size or dimension of the protective sheath part may be configured to fit into the protection pipe.

After the insertion of the protective sheath part into the protection pipe, the endoscope or the insertion cord of the endoscope may be inserted into the protection pipe. The bending section and the distal tip unit may be inserted into the protective sheath part that is positioned inside the protection pipe. Thus, the bending section and the distal tip unit may be protected by the protective sheath part, while at least a section of the insertion cord, in particular a section not protected by the protective sheath part, is protected by the protection pipe.

The protective sheath part may radially surround the bending section and the distal tip unit and may provide an intermediate piece or part between the bending section and the distal tip unit on the one side and the protection pipe on the other side. Thus, the protective sheath part may prevent a collision or bumping of the distal tip unit against the protection pipe. The inner diameter of the protection pipe may be bigger than the outer diameter of the bending section and the distal tip unit. In related art solutions, a relative (radial) movement of the distal tip unit relative to the protection pipe was possible. Thus, the distal tip unit was able to collide with an inner surface of the protection pipe. The protective sheath part may prevent this movement and therefore preferably protects the optical module or camera module in the distal tip unit against damage caused by repeated collisions with the protection pipe.

The protective sheath part may close the distal opening of the protection pipe after insertion. Furthermore, the protective sheath part may function as/may provide the (axial) stop for the insertion of the endoscope into the protection pipe and the (axial) stop for the insertion of the protective sheath part into the protection pipe.

Preferably, an axial length of the protection pipe may be as long as or longer than an axial length of the insertion cord. Thus, the complete insertion cord may be arranged inside the protection pipe. The protection pipe may shield the insertion cord against damage or unwanted bending during transport and storage. However, it is also conceivable that only a section of the insertion cord is arranged in the protection pipe.

Preferably, the protective sheath part may comprise a press fit portion configured to form a press fit with the protection pipe. An outer diameter of the press fit portion may be configured to fit into an inner diameter of the (tubular) protection pipe. The outer diameter or the press fit portion may be bigger than the inner diameter of the (tubular) protection pipe to form the press fit between the press fit portion and the protection pipe. The press fit portion may lock the protective sheath part into its preferred/defined position in the protection pipe after insertion. Thus, the protective sheath part may be fixed in the desired position after insertion into the protection pipe. The press fit portion may preferably prevent that the protective sheath part is pushed out of the protection pipe during insertion of the distal tip unit and the bending section into the protective sheath part.

The press fit portion may be formed as a (press fit) flange extending radially outward from a portion, preferably the tube portion or element, of the protective sheath part. The press fit portion may also be a number of struts or noses extending radially outward from the, preferably tubular shaped, portion of the protective sheath part. The struts may extend in a longitudinal direction or extension of the protective sheath part and may be distanced from each other in a circumferential direction. It may be advantageous to provide the press fit portion at a distal end portion/a distal end area of the protective sheath part so that insertion of the protective sheath part into the protection pipe is not unnecessarily obstructed.

According to a preferred aspect of the present disclosure, the protective sheath part may comprise a guide portion configured to guide the protective sheath part into the protection pipe. The guide portion may extend radially outward, i.e. may be a radially outward extending portion of the protective sheath part. An outer diameter of the guide portion may be fitted to the inner diameter of the protection pipe. Preferably, the outer diameter of the guide portion may be smaller than the inner diameter of the protection pipe. However, the difference in diameters between the guide portion and the protection pipe may be only small, such that proper insertion of the guide portion without jamming is assured. Thus, the guide portion may allow smooth insertion of the protective sheath part into the protection pipe and may prevent twisting or jamming of the protective sheath part in the protection pipe during the insertion process.

Two guide portions may be provided, in particular a distal guide portion and a proximal guide portion. The guide portion may be formed as a tubular outer surface of the protective sheath part.

Preferably, the protective sheath part may comprise a distal stopper portion or element, a proximal insertion portion or element, and an intermediate tube portion or element between the distal stopper portion or element and the proximal insertion portion or element.

The distal stopper portion or element may function as an (axial) stop when inserting the protective sheath part into the protection pipe and may limit the axial movement of the protective sheath part with respect to the protection pipe during the insertion. The distal stopper portion or element may be formed as or may comprise a (stopper) flange extending radially outward. An outer diameter of the distal stopper portion or element may be essentially the same as an outer diameter of the protection pipe. Therefore, it may not be possible for the distal stopper portion or element to enter the protection pipe entirely. Thus, the distal stopper portion or element may be positioned at least partially outside, preferably adjacent to the protection pipe, while the rest of the protective sheath part (and preferably of the distal stopper portion or element) may enter the protection pipe. The distal stopper portion or element may be connected to the distal end of the protection pipe and may close the distal opening of the protection pipe.

Theoretically, during the insertion of the insertion cord of the endoscope into the protection pipe, the distal tip unit could enter the protection pipe at its proximal opening and exit the protection pipe at the distal opening of the protection pipe, in particular in case the protection pipe is shorter than the insertion cord. Thus, the distal tip unit would not be protected during storage, transport and handling. The distal stopper portion or element of the protective sheath part may preferably also limit the possible axial movement of the distal tip unit during the insertion.

The distal stopper element or portion may form the (stopper) flange covering a (distal) end of the protection pipe. Moreover, the distal stopper element or portion may comprise roundings or rounded portions at the flange portion. The roundings or rounded portions may provide a rounded distal end. The protection pipe may have sharp edges. When covered by the flange of the distal stopper element or portion and its rounding, it may be prevented that the sharp edges of the protection pipe damage a surrounding sterile barrier part.

The intermediate tube portion or element may be formed as an elongated pipe. An inner diameter of the intermediate tube portion or element may be fitted to receive the bending section and the distal tip unit. The intermediate tube portion or element may form the hole or channel for insertion of the bending section and the distal tip unit.

The proximal insertion portion or element may be configured to receive the bending section and the distal tip unit and guide the same into the protective sheath part. Thus, the proximal insertion portion or element will reduce any risk of scratching of the distal tip unit or general damage to the bending section during the insertion.

Furthermore, the proximal insertion portion or element may be cone-shaped or funnel-shaped for guiding the distal tip unit and the bending section of the endoscope into the protective sheath part. Preferably, the proximal insertion portion or element may be arranged at a proximal side of the protective sheath part. That means the proximal insertion portion or element may be arranged at the side of the protective sheath part from which the distal tip unit and the bending section are inserted.

The proximal guide portion of the protective sheath part may be positioned or arranged at the proximal insertion portion or element. Thus, an outer side or wall surface of the cone or funnel of the proximal insertion portion or element may be shaped to function as (at least a part of) the guide portion. Thus, one single portion or element of the protective sheath part may be designed to function as the guide portion and the insertion portion or element together.

The (maximum) outer diameter of the distal stopper portion or element may be bigger/greater than the outer diameter of the press fit portion. The distal stopper portion or element may not be configured to enter the protection pipe. The press fit portion in contrast may be configured to enter the protection pipe. However, the press fit portion may be moved inside the protection pipe only with a certain resistance. The outer diameter of the guide portion may be smaller than the outer diameter of the press fit portion. Thus, the guide portion may also be configured to enter the protection pipe. In contrast to the press fit portion, the guide portion may be moved inside the protection pipe with only minimal resistance.

Furthermore, the protective sheath part may be an integral part comprising a distal stopper portion, a proximal insertion portion, and an intermediate tube portion between the distal stopper portion and the proximal insertion portion. The design of the protective sheath part as the integral part may reduce assembly labor and therefore assembly costs. Low component costs may be especially advantageous for single-use endoscopes.

Preferably, the integral protective sheath part may be manufactured by molding, especially injection molding. Injection molding may allow for cost-effective and quick production of integral protective sheath parts. Injection molding may especially be preferred for high-volume production. Manufacturing by injection molding may result in low production costs per part and thus may be advantageous for single-use endoscopes.

Moreover, the press fit portion may be provided at the intermediate tube portion. Especially, when the protective sheath part is manufactured as an integral part by injection molding, it may be advantageous to position the press fit portion at the intermediate tube portion. Preferably, the press fit portion may be formed as the flange extending radially outward in an axial area of the intermediate tube portion. The flange extending radially outward may be comfortable to manufacture by injection molding.

The distal guide portion may be provided at the distal stopper portion. Thus, the distal guide portion may be positioned at a distal end section of the protective sheath part. Therefore, the distal guide portion may have a certain distance to the proximal guide portion. The two distanced guide portions may avoid a twisting or jamming of the protective sheath part during insertion in the protection pipe. For the integral protective sheath part manufactured by injection molding, the distal guide portion may be formed as an outer shoulder extending from the stopper flange in the proximal direction.

According to a preferred aspect of the present disclosure, the protective sheath part may comprise a distal stopper element, a proximal insertion element, and an intermediate tube element, wherein the distal stopper element and the proximal insertion element are both attached to the intermediate tube element. Thus, the protective sheath part may be assembled from multiple components, namely the distal stopper element, the proximal insertion element, and the intermediate tube element. It may be possible to combine different components and thus vary the length and/or the inner diameter of the protective sheath part. Therefore, the assembled protective sheath part may provide an universal solution for different endoscopes.

Preferably, the press fit portion providing the press fit engagement between the protective sheath part and the protection pipe may be provided at the distal stopper element. Said differently, the press fit portion may be arranged at an end section of the protective sheath part. Thus, it may not be necessary to shove the press fit portion in the protection pipe over a long distance. As a result, it may be easy for a user to insert the protective sheath part into the protection pipe.

Preferably, the distal stopper element may be manufactured by molding, especially injection molding. The distal stopper element may comprise a tubular receiving portion configured to receive the intermediate tube element and a stopper flange (portion) extending radially outward from the receiving portion. The distal stopper element may further comprise the press fit portion. The press fit portion may be formed as longitudinal struts/ribs extending radially outward from the receiving portion. The struts/ribs may be distanced from each other in the circumferential direction. Therefore, the press fit portion may be easily formed when manufacturing the distal stopper element.

Preferably, the proximal insertion element may be manufactured by molding, especially injection molding. The proximal insertion element may comprise a tube-shaped outer surface forming the guide portion. Thus, the proximal insertion element may combine the insertion and the guide function in one single component or element.

Moreover, the intermediate tube element may be manufactured by extrusion. Extrusion may provide a cost-effective and easy process to provide tubular structures like the intermediate tube element.

According to a preferred aspect of the present disclosure, the distal stopper element may be attached to the intermediate tube element by press fit. The proximal insertion element may also be attached to the intermediate tube element by press fit. Assembling the components or elements by press fitting provides a secure and cost-effective assembly process for the protective sheath part as no further joining material like screws or clue is required. Low assembly costs may be advantageous for single-use endoscopes.

According to another preferred aspect of the present disclosure, the protective sheath part may comprise a ventilation hole for a disinfection gas. The ventilation hole may be configured to allow the disinfection gas to reach the distal tip unit and the bending section accommodated in the protective sheath part. Before a (single) use of the endoscope, the endoscope may be disinfected. The disinfection gas may pass through the ventilation hole to the distal tip unit and the bending section.

Preferably, the endoscope packaging system may further comprise the sterile barrier part, wherein at least the insertion cord of the endoscope, the protective sheath part, and the protection pipe may be arranged inside the sterile barrier part. The sterile barrier part may be formed as a semi-permeable plastic or polymer foil. Preferably, the sterile barrier part may be manufactured from High Density Polyethylene (PE-HD), for example from Tyvek. The endoscope, the protective sheath part, and the protection pipe may all be shrink-wrapped together in the foil. The semi-permeable plastic or polymer foil of the sterile barrier part may be permeable for the disinfection gas, but may not let bacteria, viruses, fungi or parasites pass the barrier.

Preferably, the distal tip unit may comprise the camera module/imaging device. The camera module may be in risk of being damaged during transport and handling of the endoscope packaging system. Especially, repeated bumping of the camera module against the protection pipe during transport and handling could lead to damages to the camera module. Thus, the protective sheath part may limit a relative movement of the distal camera module and protect the camera module.

Preferably, the endoscope is a single-use endoscope. Single-use endoscopes are often manufactured from a polymer or plastic material. Bending sections manufactured from a polymer or plastic material may deform or age during storage in the endoscope packaging system. Thus, the protective sheath part may be especially useful for the storage and transport of such single-use endoscopes.

Preferably, the endoscope has a long and thin insertion cord. Long and thin insertion cords may be especially in danger of deformation and aging during storage and transport. The bending sections and the bending segments of long and thin insertion cords may be especially thin and prone to deformation.

Preferably, the endoscope is a ureteroscope or bronchoscope. Ureteroscopes or bronchoscopes may have especially long and thin insertion cords and accordingly may have thin bending sections. Both a ureteroscope and a bronchoscope are often one-plane bending endoscopes. A cholangioscope is an example of a two-plane bending endoscope with a relatively thin insertion cord.

BRIEF DESCRIPTION OF THE DRAWINGS

The disclosure is explained in more detail below using preferred embodiments and referring to the accompanying figures.

The figures are schematic in nature and serve only to understand the disclosure. The features of the different embodiments can be interchanged among each other.

DETAILED DESCRIPTION

Figure 1:
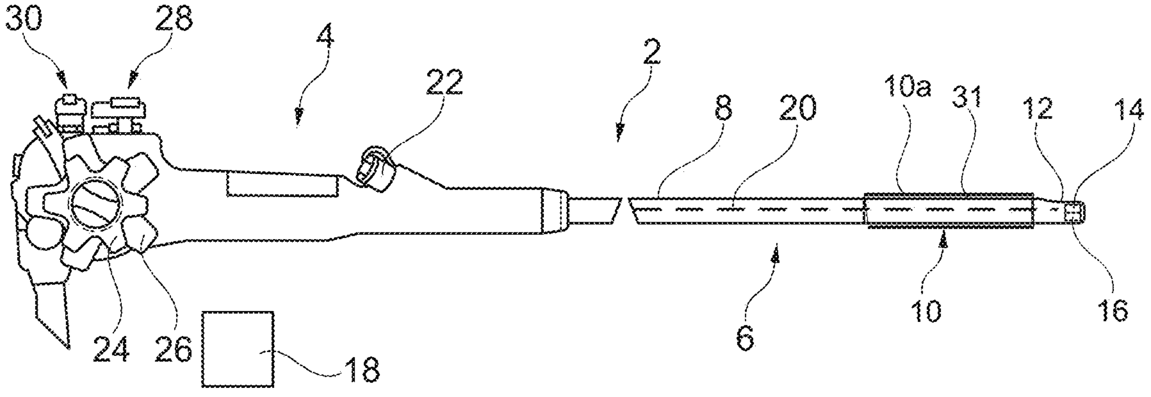
FIG. 1 shows a side view of an endoscope of an endoscope packaging system according to the present disclosure.
Figure 7:
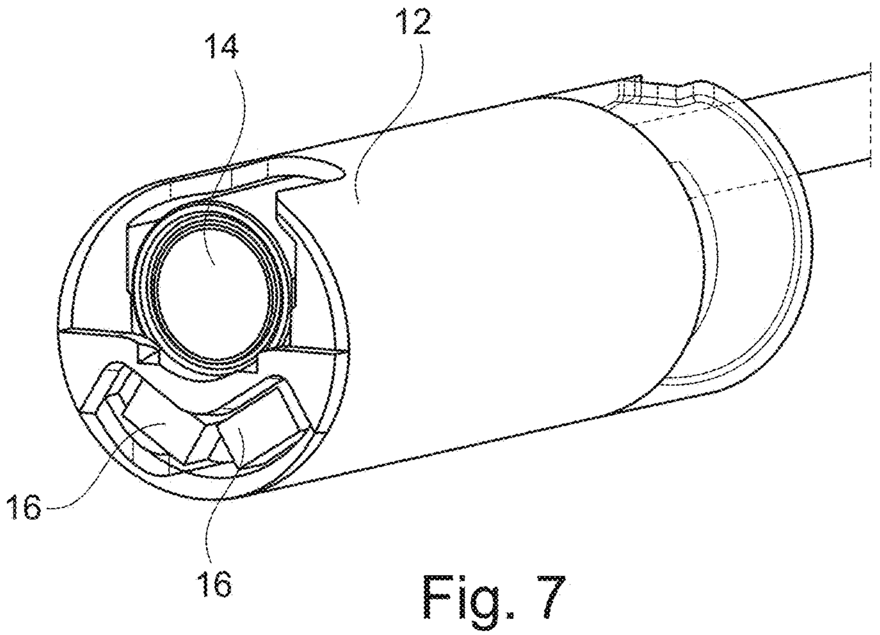
FIG. 7 shows a distal tip.

FIG. 1 shows an endoscope 2, preferably a single-use endoscope. The endoscope 2 comprises a handle or interface 4. The handle is designed to be held by a user and configured to accommodate operating parts of the endoscope 2. The interface may be connected to a robotic and manipulated remotely. The endoscope 2 further comprises an insertion cord 6 extending from the handle or interface and configured to be inserted into a patient's body cavity. The insertion cord 6 comprises an insertion tube 8, a bending section 10 and a distal tip, or tip unit, 12, which extend in this order from the endoscope handle 4. The bending section 10 includes a main body 31 and sleeve 10*a* covering the main body 31. The distal tip 12 comprises a tip housing 12*a* accommodating a light emitting device 14 and an imaging device 16, so that the patient's body cavity can be illuminated and inspected. An example of a distal tip 12 is shown in FIG. 7. Pictures/videos captured by the imaging device 16 can be shown on a monitor 18, which is provided separately from and connectable with the endoscope 2 via a cable or wirelessly. The endoscope 2 has an internal working channel 20, which is accessible via an access port 22 and via which a surgical tool or instrument can be guided into the patient's body cavity. The light emitting device 14 may comprise, for example, one or more light emitting diodes (LEDs) or a distal end of a fiberoptic cable that receives light from a light source located in the handle 4 or externally of the endoscope.

The endoscope handle 4 comprises two handle wheels, namely a first handle wheel 24 and a second handle wheel 26, which are arranged coaxially and can be rotated by the user to bend the bending section 10 for steering the distal tip 12. In particular, one of the handle wheels 24, 26, e.g. the first handle wheel 24, can be operated by the user to bend the bending section 10 in a first bending plane (e.g. in an up-and-down direction) and the other one of the handle wheels 24, 26, e.g. the second handle wheel 26, can be operated by the user to bend the bending section 10 in a second bending plane (e.g. in a right-and-left direction). The first bending plane is preferably perpendicular to the second bending plane. The endoscope 2 shown in FIG. 1 is thus a two-plane bending endoscope. It is to be understood that the endoscope 2 may also be a one-plane bending endoscope.

The endoscope handle 4 further comprises two valves, namely a gas/water injection valve 28 and a suction valve 30. The gas/water injection valve 28 and the suction valve 30 are arranged side by side on a top surface of a housing of the endoscope handle 4.

Figure 8:
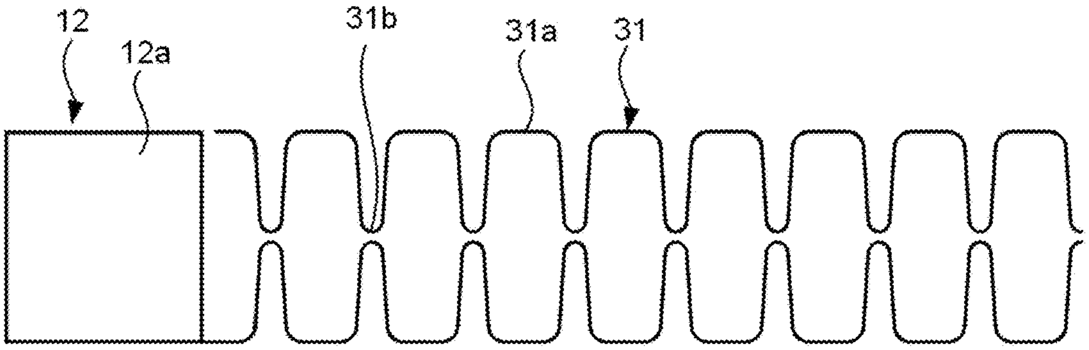
FIG. 8 shows a single-plane bending section body.
Figure 9:
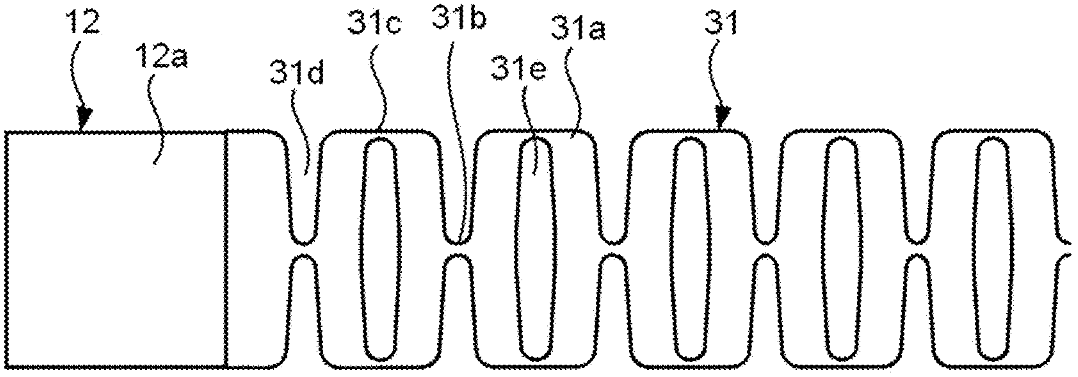
FIG. 9 shows a two-plane bending section body.

Referring to FIGS. 8 and 9, the main body 31 of the bending section 10 may be molded in one single piece or two single pieces of a polymer material. The main body 31 of such a single-use endoscope may comprise a number of bending segments 31*a* kept together by bendable hinges 31*b*. Between adjacent bending segments of the bending section body, two or three hinge members or hinge parts may be provided, which are arranged approximately diametrically opposed with respect to a center axis of the bending section body. The hinge members may e.g. be formed as foil hinges, i.e. as short strips of bendable bridges of material between adjacent bending segments allowing the material to bend in an elastic manner between adjacent bending segments. The main body 31 is made from a polymer material, in particular a thermoplastic material, and is molded, especially injection-molded. A distal segment is connected to the housing 12*a* of the distal tip 12. FIG. 8 shows a single-plane bending section and FIG. 9 shows a two-plane bending section, comprising the hinges 31*b* to articulate the bending section in one plane and hinges 31*c* to articulate the bending section in a second plane. Cut-outs 31*d* and 31*e* allow articulation of adjacent segments along one or the other plane.

Figure 2:
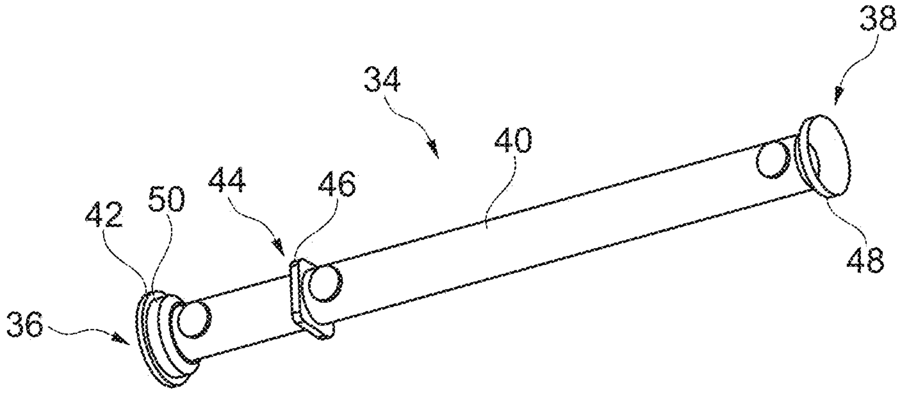
FIG. 2 shows a perspective view of a protective sheath part of the endoscope packaging system according to a first embodiment of the present disclosure.

FIG. 2 shows a perspective view of a protective sheath part 34 of an endoscope packaging system 32 according to a first embodiment of the present disclosure. The protective sheath part 34 comprises a distal stopper portion 36, a proximal insertion portion 38, and an intermediate tube portion 40. The distal stopper portion 36 comprises a stopper flange 42 extending radially outward from the intermediate tube portion 40. The protective sheath part 34 further comprises a press fit portion 44. The press fit portion 44 is formed as a press fit flange 46 extending radially outward from the tube portion 40. The proximal insertion portion 38 is cone-shaped or funnel-shaped and configured to receive the bending section 10 and the distal tip 12 of the endoscope 2. The proximal insertion portion 38 prevents damage or scratching of the bending section 10 and the distal tip 12 during insertion into the protective sheath part 34. The proximal insertion portion 38 extends radially outward from the intermediate tube portion 40 and its outer surface or shape forms a proximal guide portion 48. Adjacent to the stopper flange 42, a distal guide portion 50 is provided. The distal guide portion 50 is formed as a circumferential shoulder with a bigger outer diameter than the intermediate tube portion 40. The protective sheath part 34 shown in FIG. 2 is formed as an integral part and is preferably manufactured by injection molding.

Figure 3:
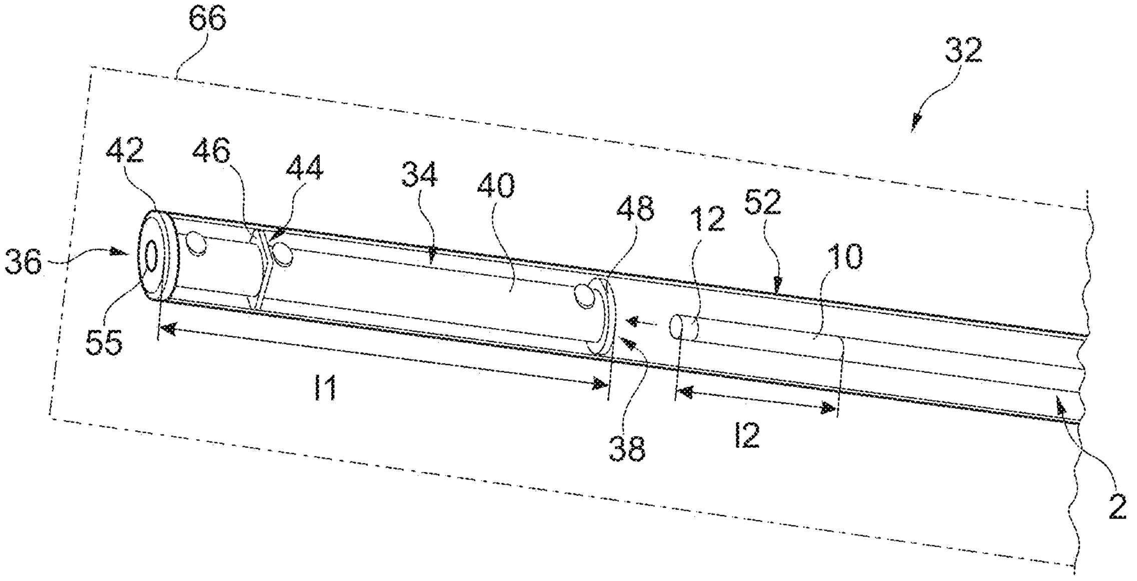
FIG. 3 shows a perspective view of the endoscope packaging system according to the first embodiment of the present disclosure.

FIG. 3 shows the endoscope packaging system 32. The protective sheath part 34 is inserted into a protection pipe 52. The protection pipe 52 is formed as a polymer tube with openings at both ends of the tube. The protection pipe 52 is preferably made from a transparent material. The protective sheath part 34 is inserted into the protection pipe 52 from a distal opening of the protection pipe 52. The distal opening or distal side of the protection pipe 52 is to be understood as the side opposite to the side from which the endoscope is inserted. The stopper flange 42 of the distal stopper portion 36 limits the (axial) insertion of the protective sheath part 34 into the protection pipe 52 as its outer diameter is bigger than an inner diameter of the protection pipe 52. Thus, the stopper flange 42 does not enter the protection pipe 52. The stopper flange 42 connects to the distal end of the protection pipe 52 and closes the distal opening of the protection pipe 52. Preferably, the outer diameter of the stopper flange 42 is as big as an outer diameter of the protection pipe 52.

The proximal guide portion 48 guides the protective sheath part 34 into the protection pipe 52. Right before the stopper flange 42 limits the insertion of the protective sheath part 34 into the protection pipe 52, the distal guide portion 50 enters the protection pipe 52. The proximal guide portion 48 and the distal guide portion 50 form together a common guide portion preventing a twisting or jamming of the protective sheath part 34 during insertion into the protection pipe 52. An outer diameter of the proximal guide portion 48 and the distal guide portion 50 is approximately the same as the inner diameter of the protection pipe 52.

An outer diameter of the press fit portion 44 is configured to form a press fit with the inner diameter of the protection pipe 52. Thus, the press fit portion 44 provides a certain resistance during insertion and needs to be pushed along the protection pipe 52. The press fit portion 44 secures the protective sheath part 34 in its position in the protection pipe 52.

After the insertion of the protective sheath part 34 into the protection pipe 52, the endoscope 2 is inserted into a proximal opening of the protection pipe 52. The bending section 10 and the distal tip 12 of the endoscope 2 are inserted into the insertion portion 38 of the protective sheath part 34. An insertion direction of the endoscope 2 is indicated schematically with an arrow in FIG. 3. The insertion of the bending section 10 and the distal tip 12 is limited by the stopper flange 42. The inner diameter of the intermediate tube portion 40 keeps the bending section 10 straight. The protective sheath part 34 has an axial length l1. The axial length l1 extends from the distal stopper portion 36 to the proximal insertion portion 38, i.e. over the entire axial length of the protective sheath part 34. The bending section 10 and the distal tip 12 have a combined axial length l2. The axial length l1 of the protective sheath part 34 is longer than the axial length l2 of the bending section 10 and the distal tip 12 combined. Thus, the bending section 10 and the distal tip 12 fit into the protective sheath part 34 completely. The axial length l1 of the protective sheath part 34 is smaller than an axial length of the insertion cord 8.

The endoscope packaging system 32 further comprises a sterile barrier part 66. The sterile barrier part 66 surrounds the protection pipe 52 with the protective sheath part 34 and the endoscope 2. The sterile barrier part 66 e.g. is a semi-permeable polymer foil. The protection pipe 52 with the inserted protective sheath part 34 and the endoscope 2 may be shrink-wrapped together in the foil.

The protective sheath part 34 may comprise a ventilation hole 55 through which disinfection gas such as ETO (ethylenoxid) may pass. The ventilation hole 55 is e.g. provided at the distal end of the distal stopper element 36. Before the (single) use of the endoscope 2, the endoscope packaging system 32 may be disinfected using the disinfection gas. The disinfection gas can pass the (semi-permeable) sterile barrier part 66 and reach the bending section 10 and the distal tip 12 embedded in the protective sheath part 34 through the ventilation hole 55. The ventilation hole 55 is preferably smaller than the diameter of the distal tip 12 such that the distal tip 12 does not pass through the ventilation hole 55 during insertion into the protective sheath part 34. Optionally, the ventilation hole 55 can be positioned on any other suitable portion of the protective sheath part 34.

Figure 4:
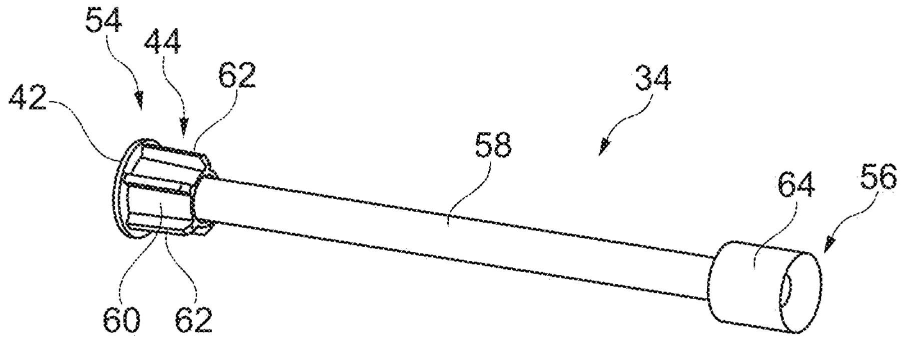
FIG. 4 shows a perspective view of a protective sheath part of an endoscope packaging system according to a second embodiment of the present disclosure.

FIG. 4 shows a perspective view of the protective sheath part 34 according to a second embodiment. The protective sheath part 34 comprises a distal stopper element 54, a proximal insertion element 56, and an intermediate tube element 58. The distal stopper element 54 comprises a tubular receiving portion 60 configured to receive the intermediate tube element 58 and the stopper flange 42. From the receiving portion 60, the stopper flange 42 extends radially outward. A number of struts 62 extend radially outward from the receiving portion 60 and form the press fit portion 44. The struts 62 extend longitudinally along the axial direction/extension of the protective sheath part and are distanced from each other in the circumferential direction of the receiving portion 60. A radial outer end/face of the struts 62 forms a press fit with the inner diameter of the protection pipe 52. The proximal insertion element 56 is substantially tubular and has an inner cone or funnel to insert the distal tip 12 and the bending section 10 of the endoscope into. A (tubular) outer surface of the proximal insertion element 56 forms a guide portion 64. An outer diameter of the guide portion 64 is approximately as big as the inner diameter of the protection pipe 52.

Figure 5:
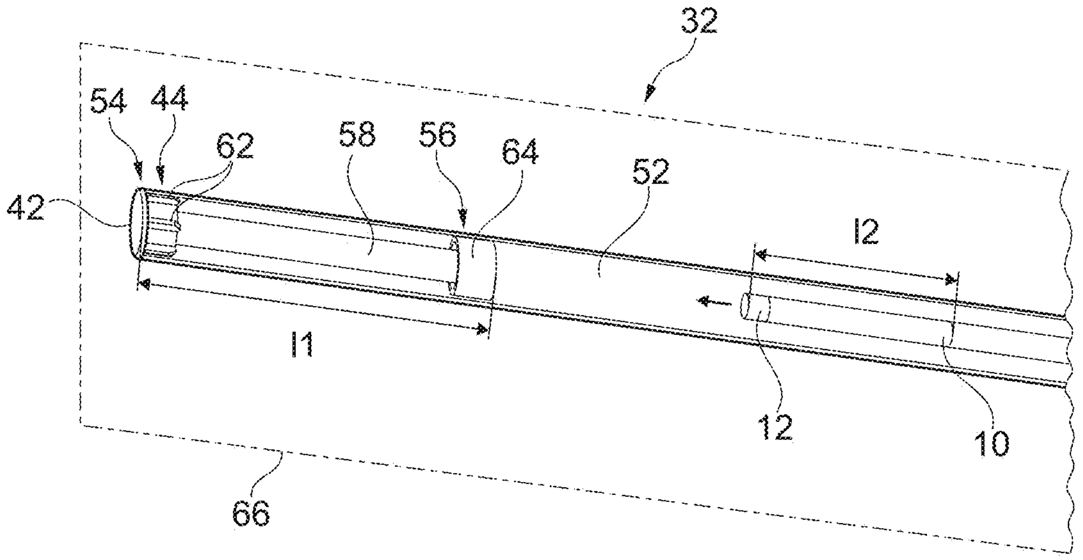
FIG. 5 shows a perspective view of the endoscope packaging system according to the second embodiment of the present disclosure.

FIG. 5 shows the protective sheath part 34 in the protection pipe 52. The protective sheath part 34 according to the second embodiment is inserted into the protection pipe 52 from the distal opening of the protection pipe 52. The guide portion 64 guides the protective sheath part 34 into the protection pipe 52 and avoids jamming or twisting of the protective sheath part 34 during the insertion. The press fit portion 44 forms the press fit with the inner diameter of the protection pipe 52. As the press fit portion 44 is provided at the distal stopper element, the press fit is established at the end of the insertion process. The stopper flange 42 closes the opening of the protection pipe 52 after the protective sheath part 34 is completely inserted into the protection pipe 52. The proximal insertion element 56 is configured to receive the distal tip 12 and the bending section 10 of the endoscope 2, which are inserted into the proximal opening of the protection pipe 52. The insertion direction of the distal tip 12 and the bending section 10 is schematically indicated by the arrow in FIG. 5. The protective sheath part 34 has the axial length l1. The bending section 10 and the distal tip 12 have a combined axial length l2. The axial length l1 of the protective sheath part 34 is longer than or as long as the axial length l2 of the bending section 10 and the distal tip 12 combined.

Figure 6:
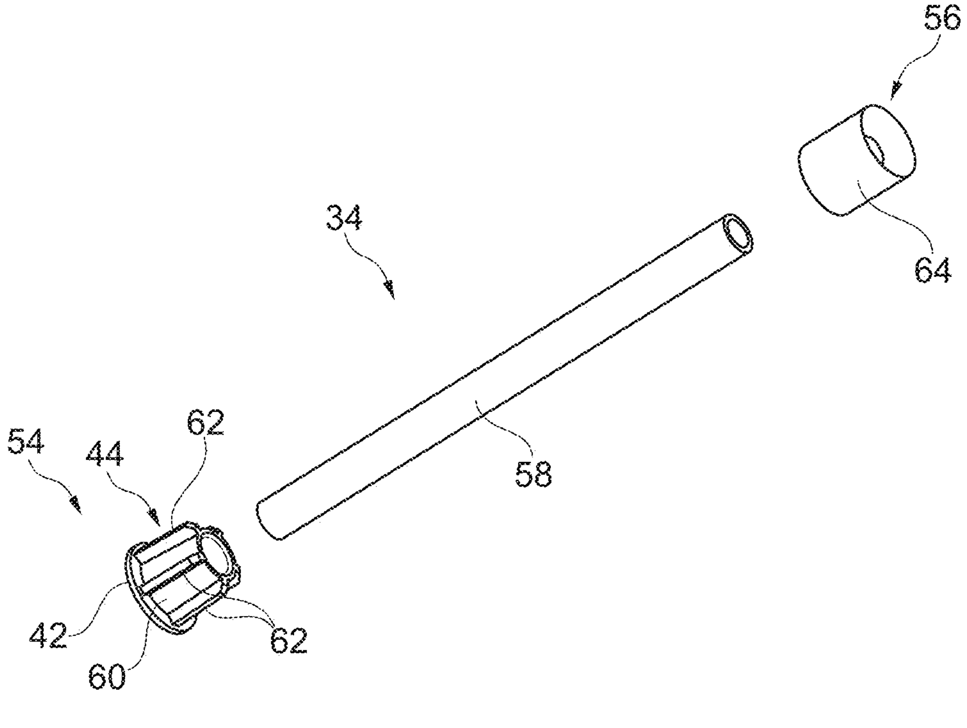
FIG. 6 shows an exploded view the protective sheath part of the endoscope packaging system according to the second embodiment of the present disclosure.

FIG. 6 shows an exploded view of the protective sheath part 34 according to the second embodiment. The distal stopper element 54 and the proximal insertion element 56 are preferably manufactured by injection molding. The press-fit portion 44 is manufactured by injection molding together with the distal stopper element 54 in one single manufacturing step. The intermediate tube element 58 is preferably manufactured by extrusion. The distal stopper element 54 and the proximal insertion element 56 are connected to the intermediate tube element 58 by a press fit to form the protective sheath part 34. The distal stopper element 54, the proximal insertion element 56, and the intermediate tube element 58 are shown in FIG. 6 before their assembly. The tubular receiving portion 60 is configured to receive the intermediate tube element 58 and is configured to form a press fit between the tubular receiving portion 60 and the intermediate tube element 58. The proximal insertion element 56 is configured to receive the intermediate tube element 58.

A connection by press fit is advantageous because no other components like screws or glue is needed for the connection of the different components. Furthermore, no threads or similar form-fitting features need to be provided at the components. However, it is also thinkable to use different joining techniques such as gluing, welding, screwing or the like to join the distal stopper element 54, the proximal insertion element 56, and the intermediate tube element 58 together.

The following items are further variations and examples of the embodiments described with reference to the figures.

1. An endoscope packaging system (1) comprising: an endoscope (2) comprising: an endoscope handle or interface (4); and an insertion cord (6) configured to be inserted into a patient's body cavity and comprising an actively bendable bending section (10) and a distal tip (12), the actively bendable bending section (10) comprising a plurality of bending segments (31) made from a polymer material; and a protective sheath part (34) configured to accommodate at least the distal tip (12) and the actively bendable bending section (10) of the insertion cord (6) of the endoscope (2) and configured to keep the bending section (10) straight during storage and transport.
2. The endoscope packaging system (1) according to item 1, wherein the actively bendable bending section (10) has an outer circumference and the protective sheath part (34) has an inner circumference, and the inner circumference of the protective sheath part (34) is adapted in size and shape to the outer circumference of the actively bendable bending section (10) so that the actively bendable bending section (10) is kept straight when accommodated in the protective sheath part (34).
3. The endoscope packaging system (1) according to items 1 or 2, wherein the protective sheath part (34) forms a hole or channel for insertion of the distal tip (12) and the actively bendable bending section (10).
4. The endoscope packaging system (1) according to any one of the preceding items 1 to 3, wherein the protective sheath part (34) forms or comprises a stop configured to prevent further insertion of the distal tip (12) and the actively bendable bending section (10), when the distal tip (12) reaches the stop.
5. The endoscope packaging system (1) according to any one of the preceding items 1 to 4, wherein the distal tip (12) and the actively bendable bending section (10) have an axial length (l2) in an axial direction of the insertion cord (6), the protective sheath part (34) has an axial length (l1), and the axial length (l1) of the protective sheath part (34) is longer than or as long as the axial length (l2) of the distal tip (12) and the actively bendable bending section (10), and is shorter than an axial length of the entire insertion cord (6).
6. The endoscope packaging system (1) according to any one of the preceding items 1 to 5, further comprising a protection pipe (52) configured to receive and accommodate the insertion cord (6) of the endoscope (2) and the protective sheath part (34).
7. The endoscope packaging system (1) according to item 6, wherein the protective sheath part (34) is an insert inserted into the protection pipe (52) and arranged radially between the insertion cord (6) of the endoscope (2) and the protection pipe (52).
8. The endoscope packaging system (1) according to items 6 or 7, wherein the protective sheath part (34) comprises a press fit portion (44) configured to form a press fit with the protection pipe (52).
9. The endoscope packaging system (1) according to any one of the preceding items 6 to 8, wherein the protective sheath part (34) comprises a guide portion (48, 50; 64) configured to guide the protective sheath part (34) into the protection pipe (52).
10. The endoscope packaging system (1) according to any one of the preceding items 1 to 9, wherein the protective sheath part (34) comprises: a distal stopper portion or element (36; 54), a proximal insertion portion or element (38; 56), and an intermediate tube portion or element (40; 58) between the distal stopper portion or element (36; 54) and the proximal insertion portion or element (38; 56).
11. The endoscope packaging system (1) according to item 10, wherein the proximal insertion portion or element (38; 56) is cone-shaped or funnel-shaped for guiding the distal tip (12) and the actively bendable bending section (10) of the endoscope (2) into the protective sheath part (34).
12. The endoscope packaging system (1) according to items 10 or 11, wherein the press fit portion (44)

providing the press fit engagement between the protective sheath part (34) and the protection pipe (52) is provided at the distal stopper element.

13. The endoscope packaging system (1) according to any one of the preceding items 1 to 12, wherein the protective sheath part (34) is an integral part comprising a distal stopper portion (36), a proximal insertion portion (38), and an intermediate tube portion (40) between the distal stopper portion (54) and the proximal insertion portion (56).
14. The endoscope packaging system according to any one of the preceding items 1 to 12, wherein the protective sheath part (34) comprises a distal stopper element (54), a proximal insertion element (56), and an intermediate tube element (58), wherein the distal stopper element (54) and the proximal insertion element (56) are both attached to the intermediate tube element (58).
15. The endoscope packaging system (1) according to item 14, wherein the distal stopper element (54) and/or the proximal insertion element (56) is manufactured by molding, especially injection molding, the intermediate tube element (58) is manufactured by extrusion and the distal stopper element (54) and/or the proximal insertion element (56) is attached to the intermediate tube element (58) by press fit.

LIST OF REFERENCE SIGNS

1 endoscope packaging system
2 endoscope
4 endoscope handle or interface
6 insertion cord
8 insertion tube
10 bending section
12 distal tip
14 light emitting device
16 imaging device
18 monitor
20 working channel
22 access port
24 first handle wheel
26 second handle wheel
28 gas/water injection valve
30 suction valve
32 endoscope packaging system
34 protective sheath part
36 distal stopper portion
38 proximal insertion portion
40 intermediate tube portion
42 stopper flange
44 press fit portion
46 press fit flange
48 proximate guide portion
50 distal guide portion
52 protection pipe
54 distal stopper element
55 ventilation hole
56 proximal insertion element
58 intermediate tube element
60 receiving portion
62 strut
64 guide portion
66 sterile barrier part
l1 axial length of the protective sheath part
l2 axial length of the bending section and the distal tip

The invention claimed is:

1. An endoscope packaging system comprising:

an endoscope including a handle and an insertion cord, the insertion cord configured to be inserted into a patient's body cavity and comprising an insertion tube coupled to the handle, a bending section and a distal tip, the bending section positioned between the insertion tube and the distal tip and being actively bendable;

a protection pipe comprising a tube with an inner surface defining a longitudinal channel configured to receive the insertion cord, the longitudinal channel comprising a proximal end and a distal end; and a protective sheath part configured for insertion into the distal end of the protection pipe and configured to receive, after said insertion into the protection pipe, the distal tip and the bending section of the insertion cord, the protective sheath part being shorter than the insertion cord and including:

an intermediate tube portion comprising a proximal end, a distal end, and a cavity extending from the proximal end to the distal end of the intermediate tube portion, the cavity being sized to accommodate the distal tip and the bending section and delimit bending of the bending section to keep the bending section straight;

a proximal insertion portion at the proximal end of the intermediate tube portion, the proximal insertion portion comprising an inwardly converging internal surface extending distally from a peripheral rim to a central opening, the internal surface tapering such that a cross-sectional dimension decreases from the peripheral rim toward the central opening, the peripheral rim being sized to slide and guide the protective sheath part into the longitudinal channel of the protection pipe, the internal surface being configured to guide the distal tip and the bending section toward the central opening; and a distal stopper portion at the distal end of the intermediate tube portion, the distal stopper portion comprising a flange and a guide portion proximal of the flange, the guide portion being configured to slide into the longitudinal channel of the protection pipe, and the flange comprising a transverse cross-section larger than a transverse cross-section of the longitudinal channel of the protection pipe to position the flange adjacent to but outside of the protection pipe.

2. The endoscope packaging system of claim 1, wherein the bending section has an outer circumference and the protective sheath part has an inner circumference configured in size and shape to the outer circumference of the bending section so that the bending section is kept straight when accommodated in the protective sheath part.

3. The endoscope packaging system of claim 1, wherein the protective sheath part comprises a proximal end and a distal end, the proximal end comprising a hole for insertion of the distal tip and the bending section, and the distal end comprising a stop and a ventilation hole, the stop configured to prevent further insertion of the distal tip and the bending section when the distal tip reaches the stop, the guide portion configured to prevent radial movement of the distal stopper portion relative to the distal end of the protection pipe, and the ventilation hole establishing fluid communication between a volume outside the protection pipe and a volume inside the protection pipe.

4. The endoscope packaging system of claim 1, wherein the intermediate tube portion comprises an outer surface having a diameter smaller than the peripheral rim.

5. The endoscope packaging system of claim 1, wherein the protective sheath part comprises, at the distal stopper portion, a press fit portion providing a press fit engagement between the protective sheath part and the protection pipe.

6. The endoscope packaging system of claim 1, wherein the distal stopper portion of the protective sheath part comprises a stop configured to prevent further insertion of the distal tip and the bending section when the distal tip reaches the stop.

7. The endoscope packaging system of claim 1, wherein the distal tip and the bending section together have an axial length in an axial direction of the insertion cord, wherein the protective sheath part has an axial length, and wherein the axial length of the protective sheath part is longer than or as long as the axial length of the distal tip and the bending section, and is shorter than an axial length of the insertion cord.

8. The endoscope packaging system of claim 1, wherein the protective sheath part is arranged radially between the insertion cord and the protection pipe.

9. The endoscope packaging system of claim 8, wherein the protective sheath part comprises a press fit portion configured to form a press fit with the protection pipe.

10. The endoscope packaging system of claim 1, wherein the guide portion is configured to guide the protective sheath part into the protection pipe and comprises a cylindrical collar.

11. The endoscope packaging system of claim 1, wherein the protective sheath part is an integral one-piece part comprising the distal stopper portion, the proximal insertion portion, and the intermediate tube portion.

12. The endoscope packaging system of claim 1, wherein wherein the distal stopper portion and the proximal insertion portion are both attached to the intermediate tube element of the protective sheath part.

13. The endoscope packaging system of claim 12, wherein the distal stopper portion and/or the proximal insertion portion is manufactured by injection molding, the intermediate tube portion is manufactured by extrusion and the distal stopper portion and/or the proximal insertion portion is attached to the intermediate tube portion by press fit.

14. The endoscope packaging system of claim 1, wherein the guide portion adjacent to the flange comprises struts extending radially outward.

15. The endoscope packaging system of claim 14, wherein the protective sheath part includes press fit portion comprising the struts.

16. The endoscope packaging system of claim 1, wherein the protection pipe is at least as long as the insertion cord and is configured to protect the insertion cord against damage.

17. The endoscope packaging system of claim 1, wherein protective sheath part comprises a press fit portion intermediate the proximal insertion portion and the distal stopper portion, the press fit portion extending radially outward from the tube portion and configured to form a press fit with the inner surface of the protection pipe.

18. The endoscope packaging system of claim 17, wherein the press fit portion comprises a flange with contact portions sized to contact the inner surface of the protection pipe.

19. The endoscope packaging system of claim 18, wherein the flange comprises non-contact portions intermediate the contact portions.

* * * * *